(12) United States Patent
Johnson

(10) Patent No.: US 8,624,029 B2
(45) Date of Patent: Jan. 7, 2014

(54) LIPIDATED IMIDAZOQUINOLINE DERIVATIVES

(75) Inventor: David A. Johnson, Hamilton, MT (US)

(73) Assignee: GlaxoSmithKline Biologicals S.A., Rixensart (BE)

( * ) Notice: Subject to any disclaimer, the term of this patent is extended or adjusted under 35 U.S.C. 154(b) by 298 days.

(21) Appl. No.: 13/125,342

(22) PCT Filed: Oct. 23, 2009

(86) PCT No.: PCT/US2009/061867
§ 371 (c)(1),
(2), (4) Date: Apr. 21, 2011

(87) PCT Pub. No.: WO2010/048520
PCT Pub. Date: Apr. 29, 2010

(65) Prior Publication Data
US 2011/0282061 A1      Nov. 17, 2011

Related U.S. Application Data

(60) Provisional application No. 61/108,210, filed on Oct. 24, 2008, provisional application No. 61/224,226, filed on Jul. 9, 2009, provisional application No. 61/229,933, filed on Jul. 30, 2009.

(51) Int. Cl.
*C07F 9/06*          (2006.01)
(52) U.S. Cl.
USPC .......................................................... 546/23
(58) Field of Classification Search
USPC ........................................................... 546/23
See application file for complete search history.

(56) References Cited

U.S. PATENT DOCUMENTS

| | | | |
|---|---|---|---|
| 5,663,387 A | 9/1997 | Singh | |
| 5,733,896 A * | 3/1998 | Holy et al. | 514/81 |
| 2007/0060754 A1 | 3/2007 | Lindstrom et al. | |
| 2007/0298093 A1 | 12/2007 | Konur et al. | |
| 2008/0213308 A1 | 9/2008 | Valiante et al. | |

* cited by examiner

*Primary Examiner* — Niloofar Rahmani
(74) *Attorney, Agent, or Firm* — Michael M. Conger

(57) ABSTRACT

The compounds of the subject invention are adjuvant molecules that comprise a imidazoquinoline molecule covalently linked to a phospho- or phosphonolipid group. The compounds of the invention have been shown to be inducers of interferon-a, IL-12 and other immunostimulatory cytokines and possess an improved activity profile in comparison to known cytokine inducers when used as adjuvants for vaccine antigens.

2 Claims, 10 Drawing Sheets schematic representation of study design p27-specific CD8 response p27-specific cytotoxic activity detected in vivo antigen-specific CD4 T cell response

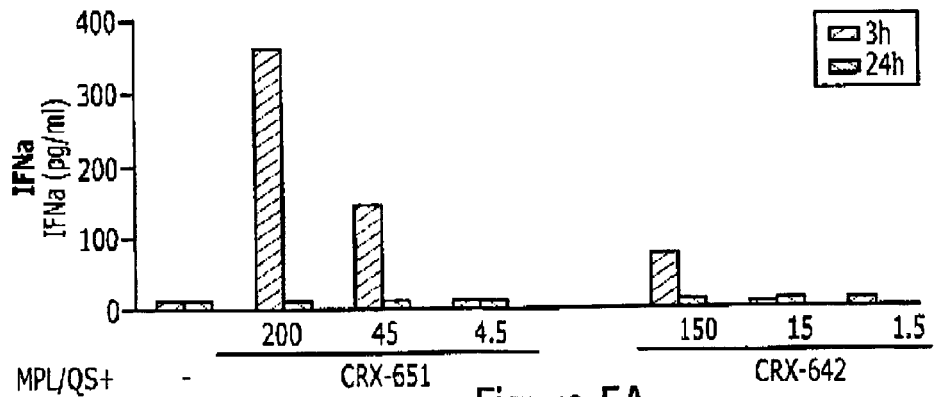

Figure 5A
serum cytokine response in groups immunized with the liposome-based formulations without (-) or with various amounts of TLR7/8 ligands together with QS21 and MPL. * not done

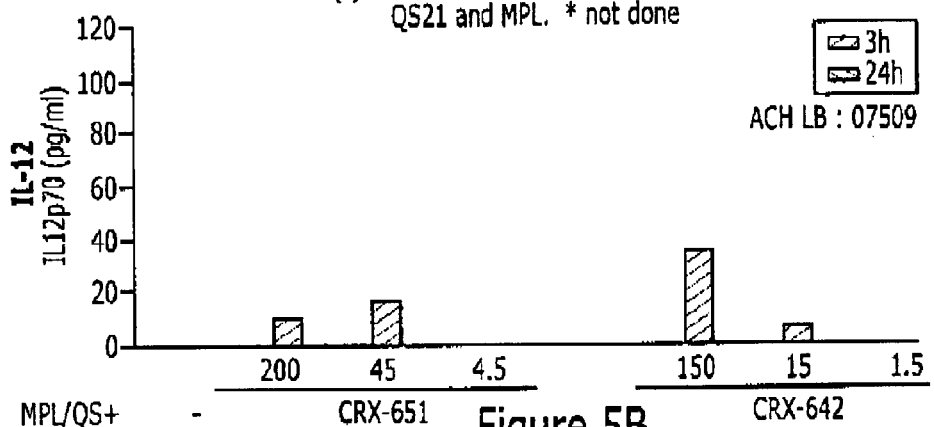

Figure 5B
serum cytokine response in groups immunized with the liposome-based formulations without (-) or with various amounts of TLR7/8 ligands together with QS21 and MPL. * not done

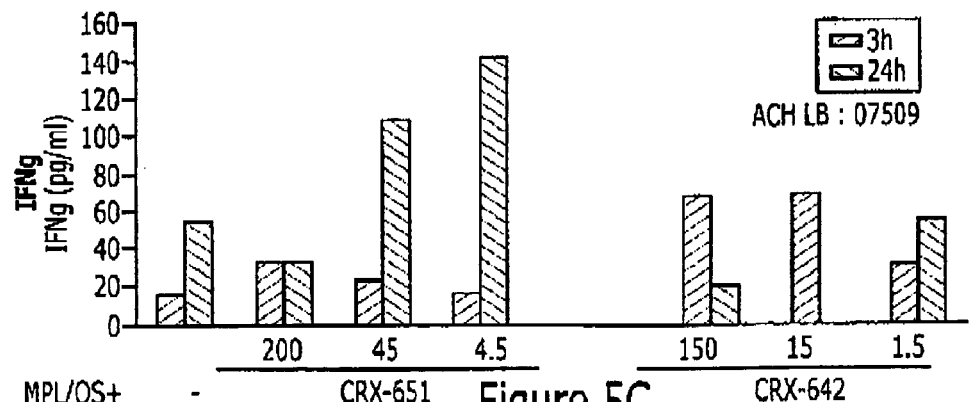

Figure 5C
serum cytokine response in groups immunized with the liposome-based formulations without (-) or with various amounts of TLR7/8 ligands together with QS21 and MPL. * not done

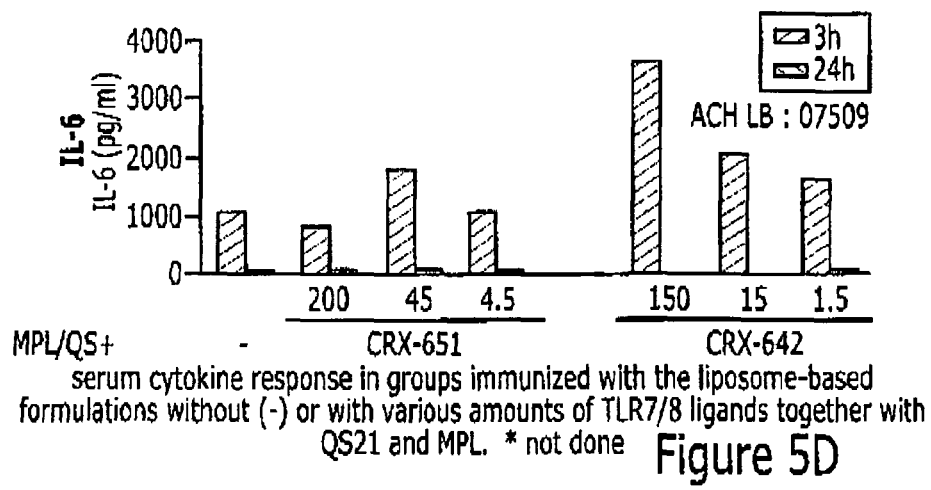

serum cytokine response in groups immunized with the liposome-based formulations without (-) or with various amounts of TLR7/8 ligands together with QS21 and MPL. * not done

Figure 5D

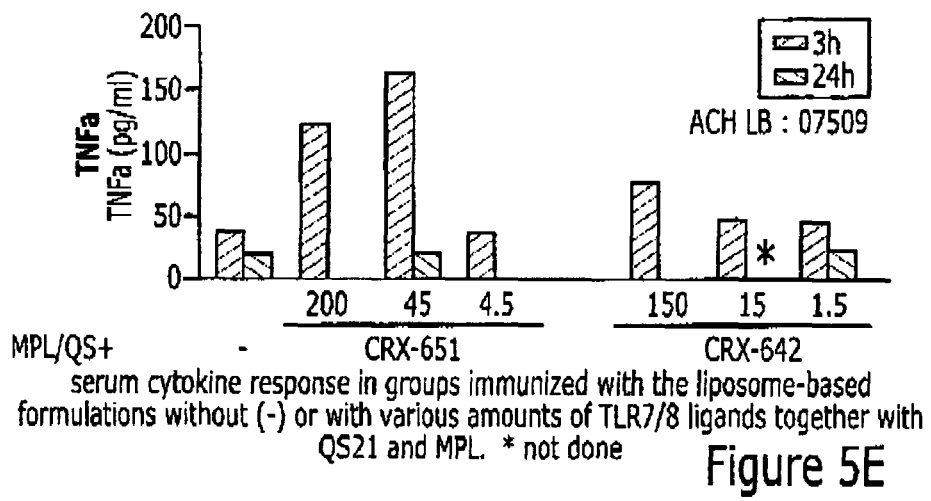

serum cytokine response in groups immunized with the liposome-based formulations without (-) or with various amounts of TLR7/8 ligands together with QS21 and MPL. * not done

Figure 5E

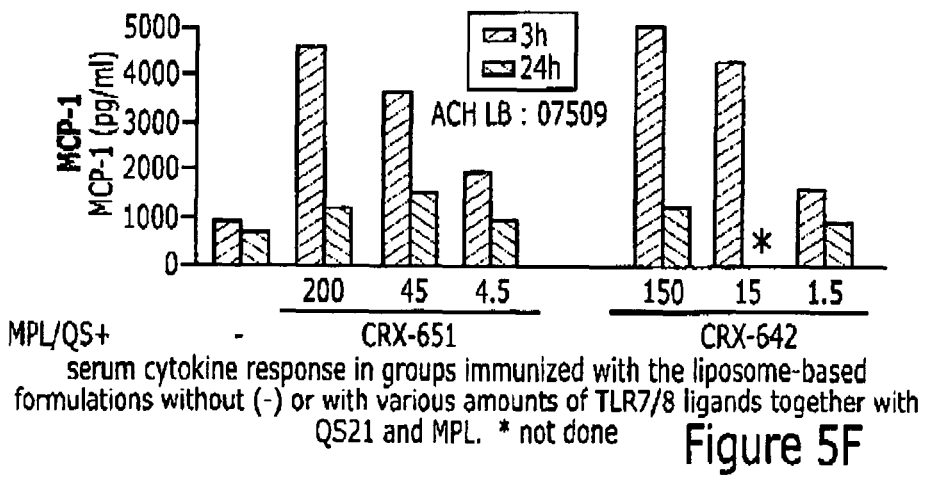

serum cytokine response in groups immunized with the liposome-based formulations without (-) or with various amounts of TLR7/8 ligands together with QS21 and MPL. * not done

Figure 5F serum cytokine response in groups immunized with the liposome-based formulations without (-) or with various amounts of TLR7/8 ligands together with QS21 and MPL. * not done

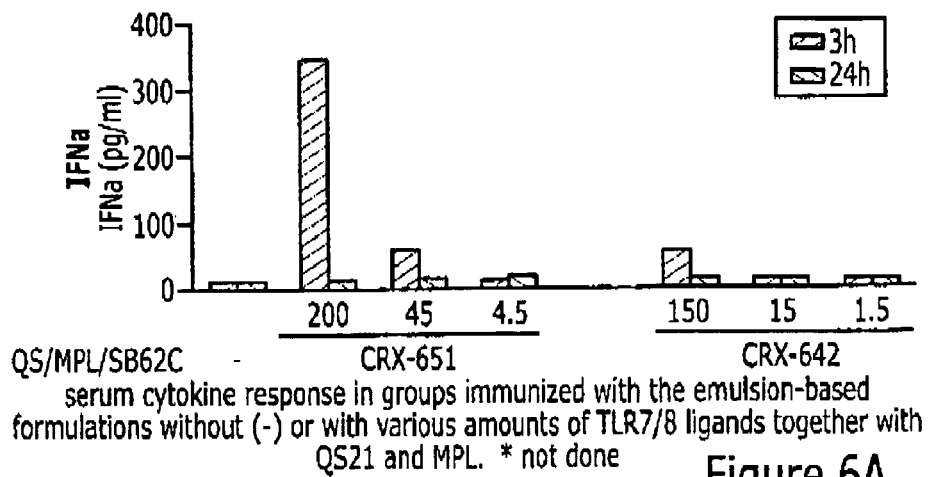

serum cytokine response in groups immunized with the emulsion-based formulations without (-) or with various amounts of TLR7/8 ligands together with QS21 and MPL. * not done

Figure 6A

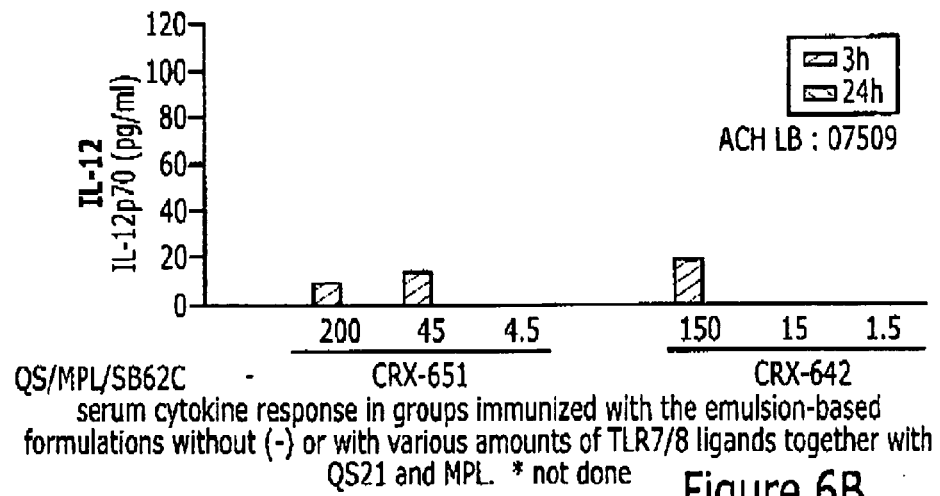

serum cytokine response in groups immunized with the emulsion-based formulations without (-) or with various amounts of TLR7/8 ligands together with QS21 and MPL. * not done

Figure 6B

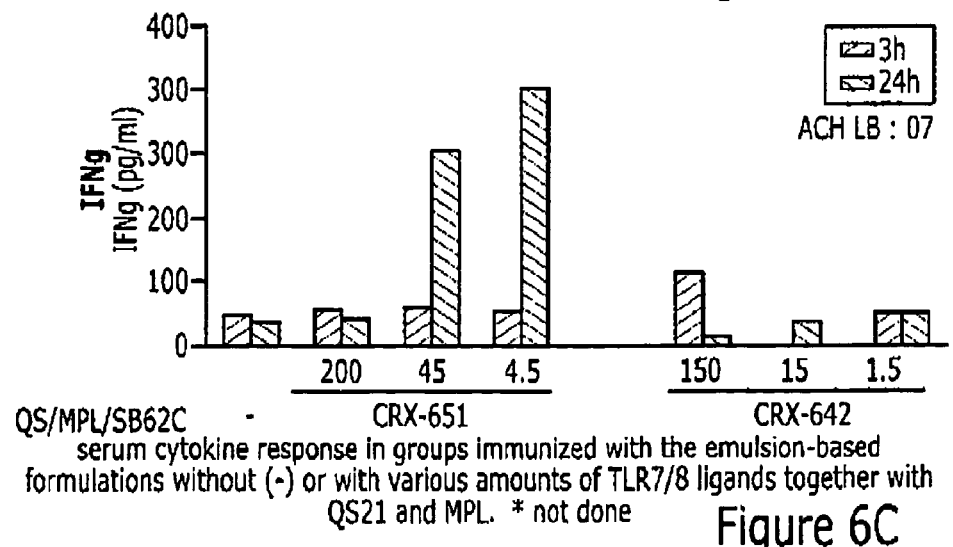

serum cytokine response in groups immunized with the emulsion-based formulations without (-) or with various amounts of TLR7/8 ligands together with QS21 and MPL. * not done

Figure 6C

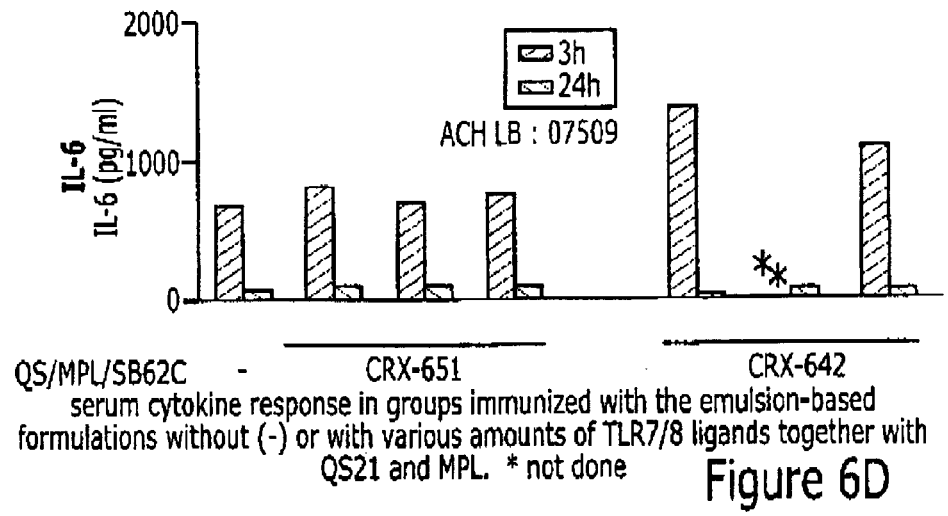

Figure 6D
serum cytokine response in groups immunized with the emulsion-based formulations without (-) or with various amounts of TLR7/8 ligands together with QS21 and MPL. * not done

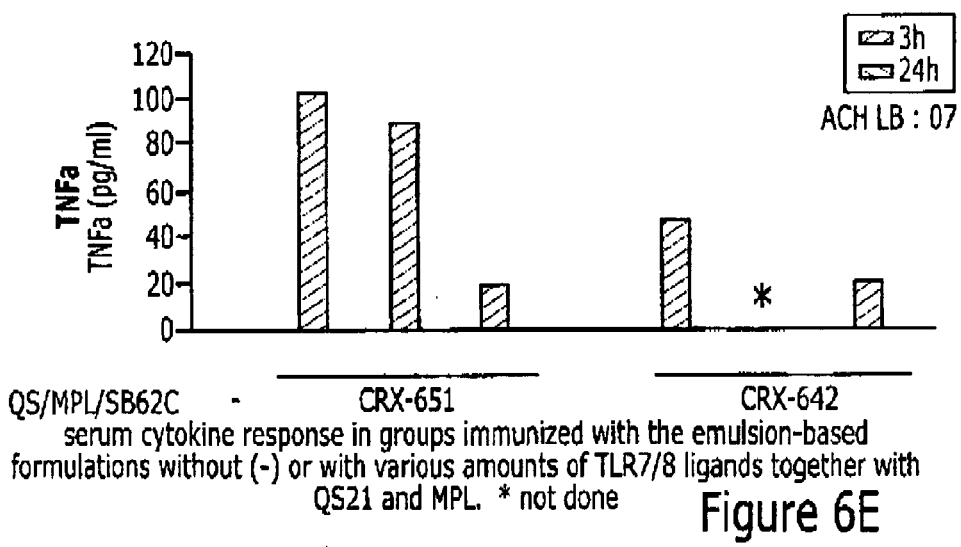

Figure 6E
serum cytokine response in groups immunized with the emulsion-based formulations without (-) or with various amounts of TLR7/8 ligands together with QS21 and MPL. * not done

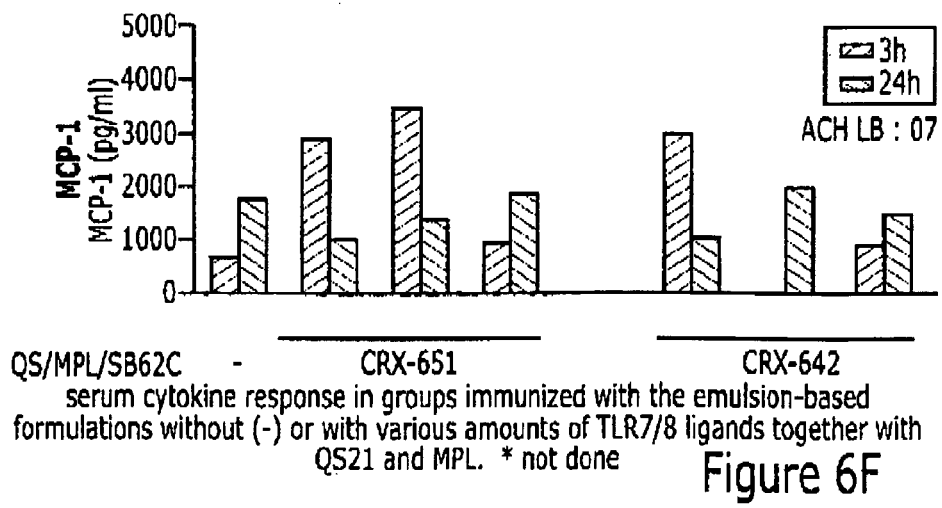

Figure 6F
serum cytokine response in groups immunized with the emulsion-based formulations without (-) or with various amounts of TLR7/8 ligands together with QS21 and MPL. * not done serum cytokine response in groups immunized with the emulsion-based formulations without (-) or with various amounts of TLR7/8 ligands together with QS21 and MPL. * not done

LIPIDATED IMIDAZOQUINOLINE DERIVATIVES

CROSS-REFERENCE TO RELATED APPLICATIONS

This application is filed pursuant to 35 USC 371 as a U.S. National Phase Application of International Patent Application Ser. No. PCT/US2009/061867 filed on Oct. 23, 2009, which claims the benefit of U.S. Provisional 61/108,210 filed Oct. 24, 2008, U.S. Provisional 61/224,226 filed Jul. 9, 2009 and U.S. Provisional 61/229,933 filed Jul. 30, 2009, each of which are incorporated herein by reference in its entirety.

BACKGROUND

The present invention relates to novel adjuvant compounds, processes for their preparation, compositions containing them, and their use as vaccine adjuvants.

The refinement and simplification of microbial vaccines and the use of synthetic and recombinant subunit antigens to improve vaccine manufacturability and safety has resulted in a decrease in vaccine potency. This has led to studies on the co-administration of adjuvants with antigens to potentiate vaccine activity and the weak immunogenicity of synthetic and recombinant epitopes. Adjuvants are additives that enhance humoral and/or cell mediated immune responses to a vaccine antigen. The design of vaccine adjuvants, however, has historically been difficult because of the complex nature of the molecular mechanisms involved in immune system function. Although the addition of microbial components has long been known to enhance adaptive immune responses, only recently was it shown that toll-like receptors (TLRs) on cells involved in immune surveillance, such as epithelial and dendritic cells, engage many of these microbial products via so-called "pathogen-associated patterns" or PAMPs. Many vaccine adjuvants and stand-alone immunomodulators appear to interact with members of the TLR family.

Of the 10 known TLRs that have been identified in humans, five are associated with the recognition of bacterial components (TLRs 1, 2, 4, 5, 6) and four others (TLRs 3, 7, 8, 9) appear to be restricted to cytoplasmic compartments and are involved in the detection of viral RNA (TLRs 3, 7, 8) and unmethylated DNA (TLR9) (Iwasaki, A., *Nat Immunol* 2004, 5, 987) Activation of TLRs regulates intracellular signaling pathways and leads to gene expression via interaction with intracellular adapter molecules such as MyD88, TRIF, TIRAP, and TRAM (Akira, S, *Nat Rev Immunol* 2004, 4, 499; Takeda, K. *Semin Immunol* 2004, 16, 3). These adapter molecules can differentially regulate the expression of inflammatory cytokines/chemokines and type I interferons (IFNa/b), which can lead to the preferential enhancement of antigen-specific humoral and cell-mediated immune responses (Zughaier, S. *Infect Immun* 2005, 73, 2940). Humoral immunity is the major line of defense against bacterial pathogens, whereas the induction of cytotoxic T lymphocytes (CTLs) appears to be crucial for protective immunity in the case of viral disease and cancer.

Currently, a group of aluminum salts known as alum are the dominant adjuvants used in human vaccines. But alum typically only enhances humoral (Th2) immunity and is generally used intramuscularly due to local toxicity by other routes (e.g., subcutaneous or intradermal inoculation leads to granulomas) (Aguilar, J. *Vaccine* 2007, 25, 3752). Other potential side effects of alum include increased IgE production, allergenicity and neurotoxicity. Thus, new safe and effective vaccine adjuvants are needed which are able to stimulate both antibody and Th1-type immune responses and that are compatible with different routes of administration and antigen formulations.

In the case of TLR7 and TLR8 activation, a few different classes of small molecule mimetics of the natural (U- and/or G-rich) viral ssRNA ligands have been identified. These include certain antiviral compounds related to oxidized guanosine metabolites (oxoguanosines), which primarily interact with TLR7 (Heil, F. *Eur J Immunol* 2003, 33, 2987; Hemmi, 2002) and derivatives of adenine which engage TLR7 and/or TLR8. The immune stimulating ability of these compounds has been attributed to the TLR/MyD88-dependent signaling pathways and the production of cytokines, including IL-6 and type I (particularly interferon-α) and II interferons. TLR7 or TLR8 activation leads to the upregulation of co-stimulatory molecules (e.g. CD-40, CD-80, CD-86) and class I and II MHC molecules on dendritic cells (DCs). DCs are the principal cells of the immune system involved in uptake and presentation of antigens to T lymphocytes. Plasmacytoid dendritic cells (pDCs), which preferentially express TLR7, are professional interferon-α producing cells; whereas mDCs express TLR8 only. TLR8 activation on mDCs leads to the preferential production of pro-inflammatory cytokines such as IL-12, TNF-a, and IFN-g and cell-mediated immunity (CMI).

One class of adenine derivatives that has received a considerable amount of attention are the 1H-imidazo[4,5-c] quinolines (IQs). The prototypical member of this class imiquimod (R847, S-26398) was found to be effective against genital papilloma virus infections, actinic keratosis, and basal cell carcinoma when applied topically in cream form. However, imiquimod has relatively low interferon-inducing activity and both oral and topical preparations are not without side-effects. In fact, serious side effects were reported in an HCV clinical trial with imiquimod. The large immunological "footprint" of TLR7 agonists in general has led concerns over toxicity: Clinical trials with another TLR7 agonist ANA-975, an oxoguanosine derivative, were recently suspended due to toxicity issues.

Another member of the IQ class of TLR7/8 ligands and a derivative of a metabolite of imiquimod is resiquimod. Resiquimod (R-848, S-28609) also activates TLR7 in macrophages and DCs in a MyD88-dependent manner either directly or indirectly via an accessory molecule and upregulates co-stimulatory molecules and MHCI/II in DCs. But in contrast to imiquimod, the more potent and toxic resiquimod is also a ligand for TLR8 signaling, which leads to the reversal of CD4+ regulatory (Treg) cell function. Using transfected HEK293 cells, it was recently shown that TLR7 agonists are more effective at generating IFN-a and IFN-regulated cytokines, whereas TLR8 agonists were more effective at inducing proinflammatory cytokines such as TNF-a and IL-12, suggesting that TLR7 activation may be more important for antibody responses (Th2-type responses) while TLR8 activation should drive CMI or Th1-type immune responses. However, as mentioned above, many TLR7/8 agonists often display toxic properties, are unstable, and/or have unsubstantial immunostimulatory effects. Thus, the discovery and development of effective and safe adjuvants that activate TLR7 and/or TLR8 is essential for improving the efficacy and safety of existing and new vaccines via helping to control the magnitude, direction, and duration of the immune response against antigens.

Unlike TLR2 and TLR4, which recognize PAMPs on cell surfaces, TLR7/8 PAMPs are sensed in the endosomal/lysosomal compartments and require endosomal maturation. Cellular uptake is prerequisite for cellular activation in the case of natural and zenobiotic TLR7/8 ligands such as imiquimod and resiquimod. Thus, strategies that would increase the penetration of the TLR7/8 ligand into DCs and other immune cells could enhance TLR activation and vaccine efficacy as well as ameliorate toxic effects.

Lipid conjugates of nucleoside drugs are known in the art to enhance oral bioavailability in general as well as permit incorporation of the resulting "nucleolipid" into lipid membranes of liposomes. Incorporating unstable and/or toxic drugs in liposomes establishes a slow-release carrier system or molecular depot, which protects the drug from degradation and decreases toxic side effects. The potency of such "lipid prodrugs" has been reported to be comparable to that of the non-derivatized drugs (U.S. Pat. No. 5,827,831—NeXstar). Depot preparations of imidazoquinolines and fatty acylated IQs have been reported in the art for the purposes of maintaining the IQ for an extended period within a localized tissue region to decrease metabolism and toxicity (WO 2005/001022—3M). However, conjugating an imidazoquinoline to a phospho- or phosphonolipid in a specific manner in order to facilitate uptake into immune cells, when administered alone or in depot formulation with an antigen, and enhance endosomal TLR7/8 activation and antigen presentation is not known in the art. Enhanced immune responses with compounds of the subject invention are possibly due to direct interaction of compounds of formula (I) with endosomal TLR7 and/or TLR8 and/or interaction of an active metabolite after enzymatic action.

BRIEF DESCRIPTION OF THE INVENTION

The compounds of the invention have been shown to be inducers of interferon-a, IL-12 and other immunostimulatory cytokines and may possess an improved activity-toxicity profile in comparison to known cytokine inducers when used as adjuvants for vaccine antigens in the therapeutic or prophylactic treatment of infectious diseases and cancer. These compounds are also novel per se.

SUMMARY OF THE INVENTION

Figure 1:
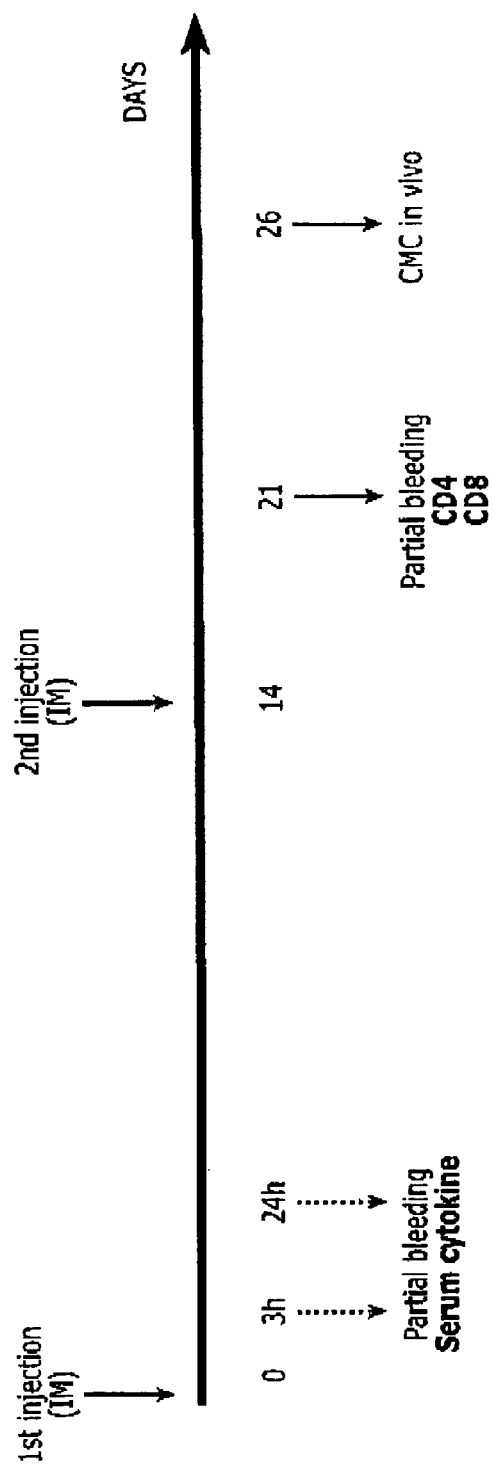
FIG. 1 shows a schematic representation of study design.

The compounds of the subject invention are adjuvant molecules that comprise a imidazoquinoline molecule which may be covalently linked to a phospho- or phosphonolipid group. The compounds of the subject invention are broadly described by Formula I:

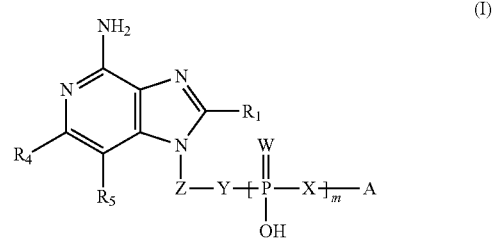

wherein
$R_1$=H, $C_{1-6}$alkyl, $C_{1-6}$alkylamino, $C_{1-6}$alkoxy, $C_{3-6}$cycloalkyl$C_{1-6}$alkyl, $C_{3-6}$cycloalkyl$C_{1-6}$alkylamino, $C_{3-6}$cycloalkyl$C_{1-6}$alkoxy, $C_{1-6}$alkoxy$C_{1-6}$alkyl, $C_{1-6}$alkoxy$C_{1-6}$alkylamino, $C_{1-6}$alkoxy$C_{1-6}$alkoxy; branched or unbranched and optionally terminally substituted with a hydroxyl, amino, thio, hydrazino, hydrazido, azido, acetylenyl, carboxyl, or maleimido group, $Z$=$C_2$-$C_6$ alkyl or alkenyl, unsubstituted or terminally substituted by —(O—$C_2$-$C_6$alkyl)$_{1-6}$—

$Y$=O, NH $X$=O, $CH_2$, $CF_2$ $W$=O or S m=1-2,

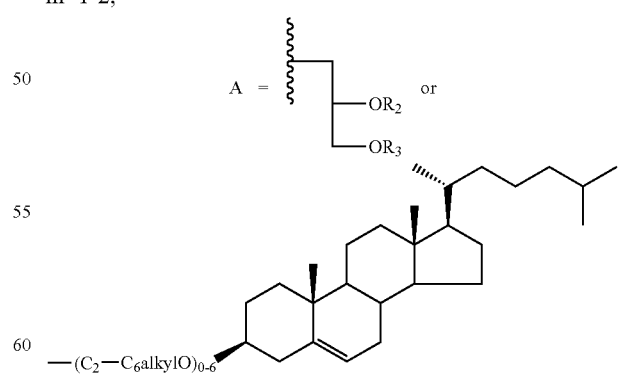

wherein
$R_2$=H or straight/branched/unsaturated $C_4$-$C_{24}$ alkyl or acyl
$R_3$=straight/branched/unsaturated $C_4$-$C_{24}$ alkyl or acyl $R_4$, $R_5$=independently H, $C_1$-$C_6$alkyl, $C_1$-$C_6$ alkoxy, halogen, or trifluoromethyl; or taken together alternatively form a 6-membered aryl, heteroaryl containing one nitrogen atom, cycloalkyl, or heterocycloalkyl ring containing one nitrogen atom; unsubstituted or substituted by one or more of $C_1$-$C_6$alkyl, $C_1$-$C_6$ alkoxy, halogen, or trifluoromethyl, or pharmaceutically acceptable salts thereof.

In one embodiment, the compounds of the subject invention are more specifically described by Formula II:

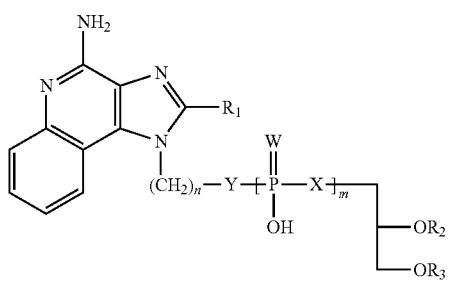

(II)

wherein $R_1$=H, $C_{1-6}$alkyl, $C_{1-6}$alkylamino, $C_{1-6}$alkoxy, $C_{3-6}$cycloalkyl$C_{1-6}$alkyl, $C_{3-6}$cycloalkyl$C_{1-6}$alkylamino, $C_{3-6}$cycloalkyl$C_{1-6}$alkoxy, $C_{1-6}$alkoxy$C_{1-6}$alkyl, $C_{1-6}$alkoxy$C_{1-6}$alkylamino, $C_{1-6}$alkoxy$C_{1-6}$alkoxy; branched or unbranched and optionally terminally substituted with a hydroxyl, amino, thio, hydrazino, hydrazido, azido, acetylenyl, carboxyl, or maleimido group, n=1-6

Y=O, NH

X=O, $CH_2$, $CF_2$

W=O or S m=1-2, $R_2$=H or straight/branched/unsaturated $C_4$-$C_{24}$ alkyl or acyl $R_3$=straight/branched/unsaturated $C_4$-$C_{24}$ alkyl or acyl (e.g. phosphatidyl, lysophosphatidyl ether or ester when W=O, X=O, m=1)

TABLE 1

| Example | Ref. No. | $R_1$ | n | m |
|---|---|---|---|---|
| 1 | — | — | — | — |
| 2 | — | — | — | — |
| 3 | L1 | H | 2 | 1 |
| 4 | L2 | n-Bu | 2 | 1 |
| 5 | L3 | $CH_2OEt$ | 2 | 1 |
| 6 | L4 | $CH_2OEt$ | 4 | 1 |
| 7 | — | — | — | — |
| 8 | L5 | $CH_2OEt$ | 2 | 2 |
| 9 | — | — | — | — |

For all Examples shown: Y = W = X = O; $R_2$ = $R_3$ = hexadecanoyl

EXAMPLE 1

General Procedure for the Preparation of 4-Amino-1-[2-(1,2-dipalmitoyl-sn-glycero-3-phospho)alkyl]-1H-imidazo[4,5-c]quinolines (Compound (I), Y=W=X=O, m=1)

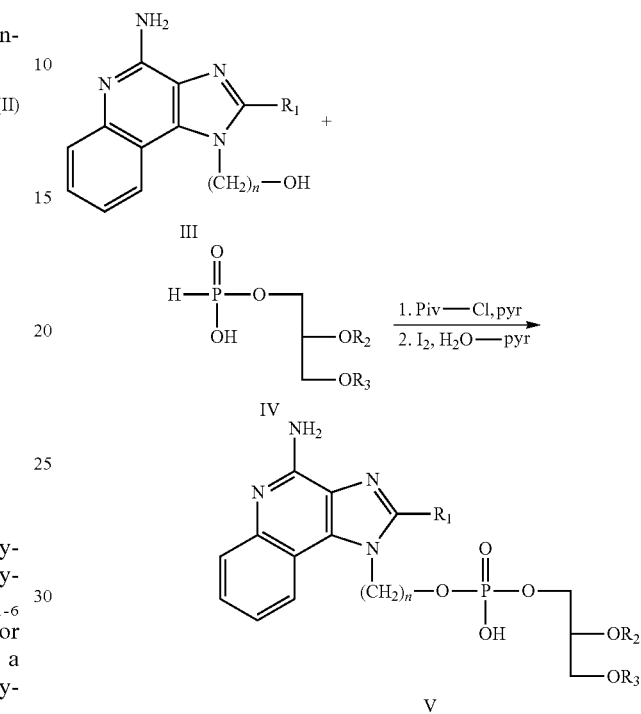

Imidazoquinoline monophosphate diglycerides V were prepared by coupling 4-amino-1-hydroxyalkyl-imidazoquinolines III (Gerster et al. *J Med Chem* 2005, 48, 3481; Izumi et al. *Bioorg Med Chem* 2003, 11, 2541) with 1-H phosphonate IV according to methods known in the art (Crossman, et al. *J Chem Soc, Perkin Trans* 1, 1997, 2769; Westerduin, et. al. *Tet Lett,* 1986, 15, 6271; Nikolaev, et al., *Carbohydr Res,* 1990, 204, 65) as follows: Imidazoquinoline III (1 eq) and H-phosphonate IV (2 eq) were suspended in n-heptane and, after evaporation of the solvent, dried overnight under high vacuum. The resulting residue was dissolved in pyridine (0.01 M compound III), treated with pivaloyl chloride (12.4 eq), and then stirred at room temperature for 6 h. A solution of iodine (4 eq) in 19:1 pyridine-water (0.04 M) was added and the resulting mixture stirred at room temperature for 1 h and then partitioned between $CHCl_3$ and 1 M aq $Na_2S_2O_5$. The layers were separated and the aqueous layer was extracted twice with $CHCl_3$. The combined organic extracts were washed with 1 M triethylammonium borate buffer (pH 8), dried ($Na_2SO_4$), and concentrated. The residue obtained was purified by flash chromatography on silica gel (gradient elution, 0→25% MeOH—$CHCl_3$) and then by reverse phase chromatography (Bakerbond C8 in $CH_3CN$ containing 1% TEA, eluting with 0→60% MeOH—$CH_3CN$ containing 1% $Et_3N$) to provide compound V as a colorless solid.

EXAMPLE 2

Preparation of 4-Amino-1-(4-hydroxybutyl)-2-ethoxymethyl-1H-imidazo[4,5-c]quinoline hydrochloride (Compound (III), $R_1$=$CH_2OCH_2CH_3$, n=4)

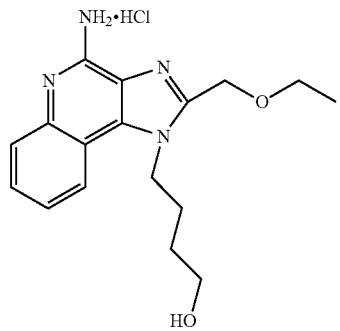

(1) A suspension of 4-hydroxy-3-nitroquinoline (Gerster et al. *J Med Chem* 2005, 48, 3481) in DMF (0.7 M) was treated dropwise with $POCl_3$ (1.2 eq) and stirred at 50° C. for 30 min. The reaction mixture was poured into ice-water and extracted twice with $CH_2Cl_2$. The combined organic layers were washed with water, dried ($Na_2SO_4$) and concentrated. The crude product obtained was added to a solution of 4-aminobutanol (1.3 eq) and triethylamine (1.9 eq) in EtOH and heated to reflux for 15 min. After concentration, flash chromatography on silica gel (gradient elution, 2→4% MeOH—$CHCl_3$) afforded 4-(4-hydroxybutyl)amino-3-nitroquinoline as a yellow solid in 97% yield.

(2) A solution of the compound prepared in (1) above in EtOAc (0.1 M) was hydrogenated in the presence of 5% Pt/C (5% w/w) and $MgSO_4$ (1.5 eq) at 50 psig for 6 h. The reaction mixture was filtered through celite and concentrated. The orange oil obtained was heated with ethoxyacetic acid (11 eq) at 150° C. for 1 h. The reaction mixture was cooled to 0° C., basified to pH 10 with conc $NH_4OH$, and extracted twice with $CH_2Cl_2$. The combined organic layers were dried ($Na_2SO_4$) and concentrated. Flash chromatography on silica gel (1:60 MeOH—$CHCl_3$) gave the ethoxyacetate derivative which was treated with 2.6 M NaOH (5.0 eq) in EtOH (0.20 M) at room temperature for 1 h. Ethanol was removed under reduced pressure and the aqueous layer was extracted several times with AcOEt and $CH_2Cl_2$. The combined organic layers were dried ($Na_2SO_4$), and concentrated. Flash chromatography on silica gel (gradient elution, 1:50→1:15 MeOH—$CHCl_3$) afforded 1-(4-hydroxybutyl)-1H-imidazo[4,5-c]quinoline as a solid in 74% yield. $^1$H NMR ($CDCl_3$, 400 MHz) δ 9.29 (s, 1H), 8.25 (dd, 2H), 7.67 (m, 2H), 4.89 (s, 2H), 4.71 (t, 2H), 3.79 (m, 2H), 3.62 (dd, 2H), 2.12 (m, 2H), 1.82 (m, 2H), 1.25 (t, 3H).

(3) A solution of the compound prepared in (2) above and peracetic acid (1.2 eq) in ethanol (0.4 M) was heated at 60° C. for 2.5 h. After concentration, the crude product obtained was purified by chromatography on silica gel (gradient elution, 1:30→1:6 MeOH—$CHCl_3$) to afford 1-(4-hydroxybutyl)-1H-imidazo[4,5-c]quinoline 5-N-oxide as a yellow solid in 94% yield (4) A suspension of the compound prepared in (3) above in $CH_2Cl_2$ (0.43 M) was treated with $NH_4OH$ (30% aq solution, 2.7 mL) followed by p-toluenesulfonyl chloride (1.0 eq) dropwise. The resulting mixture was stirred at room temperature for 1.5 h and then concentrated. Flash chromatography on silica gel (gradient elution, 1:30→1:9 MeOH—$CHCl_3$) afforded 4-amino-1-(4-hydroxybutyl)-1H-imidazo[4,5-c]quinoline as an orange solid in quantitative yield.

(5) A solution of the compound prepared in (4) above in dioxane (0.12M) at 50° C. was treated dropwise with 4N HCl in dioxane (1.5 eq) and then allowed to cool to room temperature. The solid precipitate was collected, washed with dioxane, and dried to give 4-amino-1-(4-hydroxybutyl)-1H-imidazo[4,5-c]quinoline hydrochloride salt in 89% yield: $^1$H NMR ($CDCl_3$—$CD_3OD$, 400 MHz) δ 8.13 (d, 1H), 7.97 (d, 1H), 7.65 (t, 1H), 7.55 (t, 1H), 4.89 (bs, 2H), 4.68 (m, 2H), 3.75 (m, 2H), 3.68 (dd, 2H), 2.10 (m, 2H), 1.80 (m, 2H), 1.29 (t, 3H). $^{13}$C NMR ($CDCl_3$—$CD_3OD$, 100 MHz) δ 151.9, 148.1, 135.8, 133.7, 130.2, 128.7, 125.8, 125.4, 122.5, 121.2, 118.8, 112.1, 66.8, 64.0, 60.8, 46.8, 28.6, 26.6, 14.5. HRMS calcd for [M+H]$^+$ 315.1821, found 315.1839.

EXAMPLE 3 (L1)

Preparation of 4-Amino-1-[2-(1,2-dipalmitoyl-sn-glycero-3-phospho)ethyl]-1H-imidazo[4,5-c]quinoline (Compound (I), $R_1$=H, Y=W=X=O, n=2, m=1, $R_2$=$R_3$=n-$C_{15}H_{31}CO$)

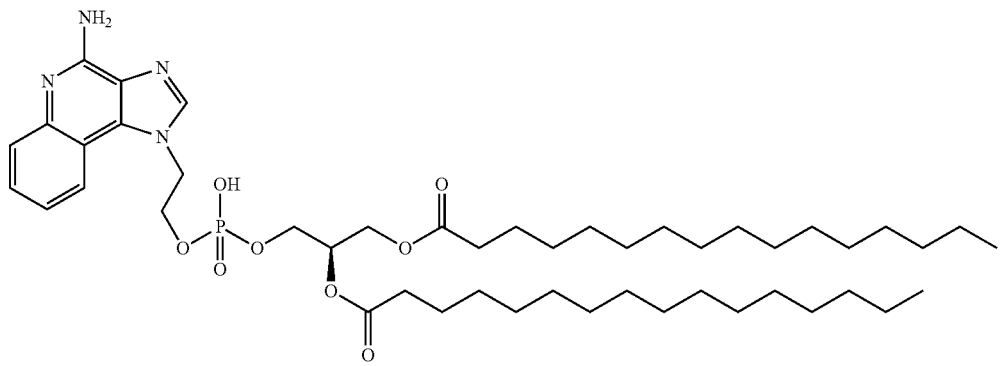 [SMILES: CCCCCCCCCCCCCCCC(=O)OC[C@H](COP(=O)(O)OCCn1cnc2c(N)nc3ccccc3c21)OC(=O)CCCCCCCCCCCCCCC]

Compound L1 was prepared in 80% yield following the general procedure described in Example 1 above: $^1$H NMR ($CDCl_3$—$CD_3OD$, 400 MHz): δ 8.22 (s, 1H), 8.16 (d, 1H), 7.41 (t, 1H); 7.21 (t, 1H), 6.92 (d, 1H), 5.26 (m, 1H), 4.82 (bs, 2H), 4.67 (bs, 2H), 4.42 (dd, 1H), 4.20 (dd, 1H), 4.05 (t, 2H), 3.14 (q, 1H), 2.31 (m, 4H), 1.59 (m, 4H), 1.25 (m, 48H), 0.88 (m, 6H); $^{13}$C NMR ($CDCl_3$—$CD_3OD$, 100 MHz): δ 173.6, 173.2, 148.1, 145.8, 134.5, 133.9, 129.3, 125.5, 124.5, 118.4, 112.3, 100.3, 77.2, 70.1, 70.0, 63.5, 62.3, 45.9, 34.1, 33.9, 31.7, 29.5, 29.5, 29.3, 29.2, 29.1, 29.1, 28.9, 28.9, 24.7, 24.7, 22.5, 13.9, 8.3. HRMS calcd for [M+H]$^+$ 859.5714, found 859.5688.

EXAMPLE 4 (L2)

Preparation of 4-Amino-1-[2-(1,2-dipalmitoyl-sn-glycero-3-phospho)ethyl]-2-butyl-1H-imidazo[4,5-c]quinoline (Compound (I), $R_1$=n-$C_4H_9$, Y=W=X=O, n=2, m=1, $R_2$=$R_3$=n-$C_{15}H_{31}CO$)

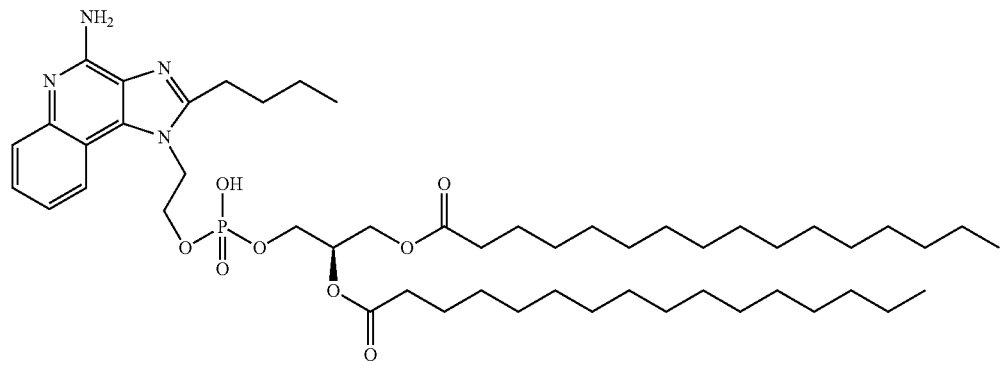 [SMILES: CCCCCCCCCCCCCCCC(=O)OC[C@H](COP(=O)(O)OCCn1c(CCCC)nc2c(N)nc3ccccc3c21)OC(=O)CCCCCCCCCCCCCCC]

Compound L2 was prepared in 78% yield following the general procedure described in Example 1 above: $^1$H NMR (CDCl$_3$—CD$_3$OD, 400 MHz): δ 8.23 (bs, 1H), 7.39 (t, 1H), 7.22 (bs, 1H), 6.93 (bs, 1H), 5.25 (m, 1H), 4.7 (bs, 2H), 4.6 (bs, 2H), 4.42 (dd, 1H), 4.19 (dd, 1H), 4.04 (t, 2H), 3.06 (bs, 2H) 2.32 (m, 4H), 1.96 (p, 2H) 1.59 (m, 6H) 1.26 (m, 48H), 1.07 (t, 3H), 0.88 (m, 6H); $^{13}$C NMR (CDCl$_3$—CD$_3$OD, 100 MHz): δ 173.6, 173.2, 157.2, 147.4, 135.2, 133.6, 128.8, 124.2, 123.6, 120.9, 118.2, 112.2, 77.2, 70.0, 69.9, 63.2, 62.2, 46.3, 33.9, 33.7, 31.6, 29.3, 29.3, 29.3, 29.1, 29.0, 28.95, 28.9, 28.8, 28.7, 28.6, 27.0, 24.5, 24.5, 22.3, 22.1, 13.6, 13.4. HRMS: calcd for [M+H]$^+$ 915.6340, found 915.6309.

EXAMPLE 5 (L3)

Preparation of 4-Amino-1-[2-(1,2-dipalmitoyl-sn-glycero-3-phospho)ethyl]-2-ethoxymethyl-1H-imidazo[4,5-c]quinoline (Compound (I), $R_1$=$CH_2OCH_2CH_3$, Y=W=X=O, n=2, m=1, $R_2$=$R_3$=n-$C_{15}H_{31}CO$)

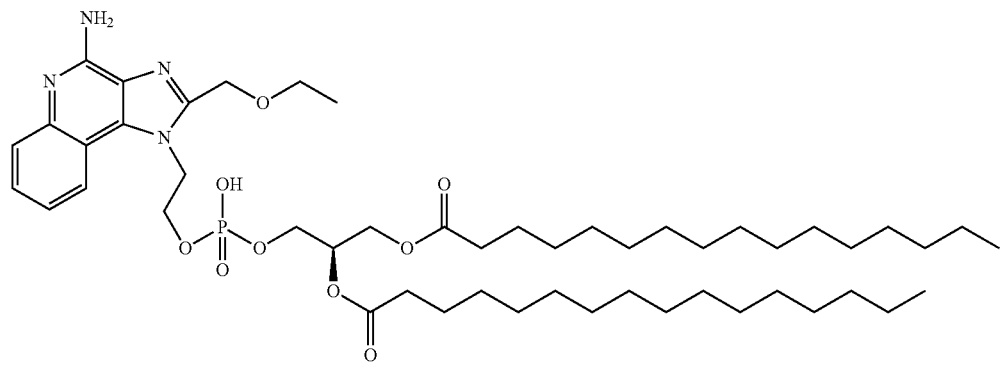 [SMILES: CCCCCCCCCCCCCCCC(=O)OC[C@H](COP(=O)(O)OCCn1c(COCC)nc2c(N)nc3ccccc3c21)OC(=O)CCCCCCCCCCCCCCC]

Compound L3 was prepared in 86% yield following the general procedure described in Example 1 above: $^1$H NMR (CDCl$_3$—CD$_3$OD, 400 MHz) δ 8.05 (bs, 1H), 7.29 (t, 1H), 7.09 (bs, 1H), 6.78 (bs, 1H), 5.11 (m, 1H), 4.80 (bs, 4H), 4.60 (bs, 2H), 4.28 (dd, 1H), 4.07 (dd, 1H), 3.90 (t, 2H), 3.54 (q, 2H), 2.18 (m, 4H), 1.59 (m, 4H), 1.16 (m, 51H), 0.76 (m, 6H); $^{13}$C NMR (CDCl$_3$—CD$_3$OD, 100 MHz): δ 173.4, 173.0, 153.3, 148.2, 135.7, 134.7, 129.1, 124.4, 124.2, 121.1, 119.1, 112.8, 77.2, 70.2, 70.2, 66.6, 65.4, 64.2, 63.5, 62.5, 57.7, 47.1, 45.7, 34.3, 34.1, 31.9, 29.7, 29.7, 29.6, 29.5, 29.3, 29.3, 29.1, 29.1, 24.9, 22.7, 15.0, 14.1, 8.6. HRMS calcd for [M+H]$^+$ 917.6132, found 917.6162.

EXAMPLE 6 (L4)

Preparation of 4-Amino-1-[2-(1,2-dipalmitoyl-sn-glycero-3-phospho)butyl]-2-ethoxymethyl-1H-imidazo[4,5-c]quinoline (Compound (I), R$_1$=H, Y=W=X=O, n=4, m=1, R$_2$=R$_3$=n-C$_{15}$H$_{31}$CO)

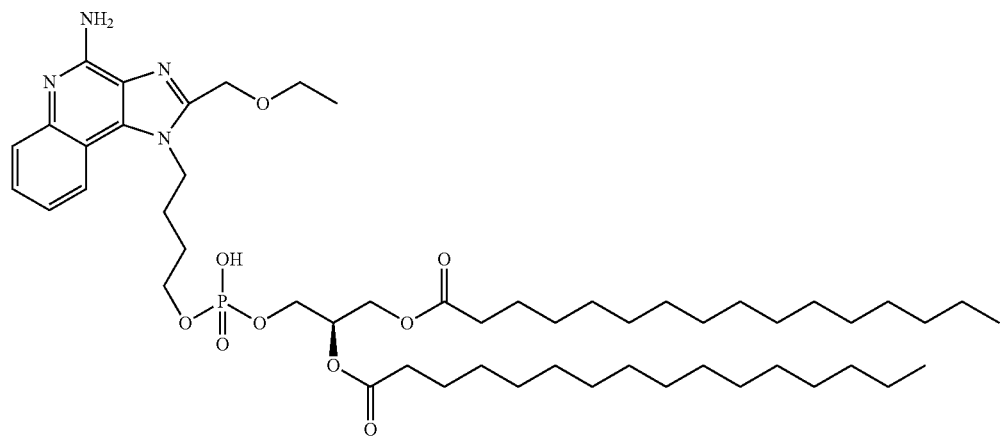 [SMILES: CCCCCCCCCCCCCCCC(=O)OC[C@H](COP(=O)(O)OCCCCn1c(COCC)nc2c(N)nc3ccccc3c21)OC(=O)CCCCCCCCCCCCCCC]

Compound L4 was prepared in 26% yield following the general procedure described in Example 1 above: $^1$H NMR (CDCl$_3$, 400 MHz): δ 11.2 (bs, 1H), 7.78 (d, 1H), 7.30 (t, 1H), 7.20 (d, 1H), 6.78 (t, 1H), 6.39 (bs, 1H), 5.28 (m, 1H), 4.79 (s, 2H), 4.43-4.50 (m, 3H), 4.11-4.27 (m, 5H), 3.67 (dd, 2H), 2.41 (bs, 2H), 2.30 (dd, 4H), 1.96 (bs, 1H), 1.60 (m, 4H), 1.25 (m, 54H), 0.88 (1, 6H); $^{13}$C NMR (CDCl$_3$, 100 MHz): δ 173.4, 173.0, 150.9, 148.9, 134.7, 134.2, 128.0, 124.3 (2), 120.5, 118.4, 111.8, 70.3, 70.2, 66.8, 64.7, 64.4, 64.3, 63.4 (2), 62.4, 46.6, 34.2, 34.1, 31.9, 29.6 (3), 29.4, 29.3 (2), 29.2, 29.1, 28.2, 27.4, 24.8 (2), 22.6, 15.1, 14.1. HRMS calcd for [M−H]$^−$ 943.6289, found 943.6251.

EXAMPLE 7

General Procedure for the Preparation of 4-Amino-1-[2-(1,2-dipalmitoyl-sn-glycero-3-diphospho)alkyl]-1H-imidazo[4,5-c]quinolines (Compound (I), Y=W=X=O, m=2)

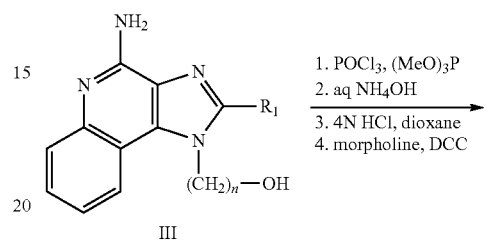

-continued

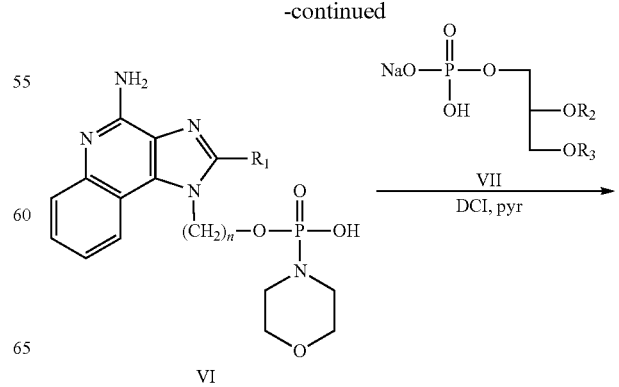

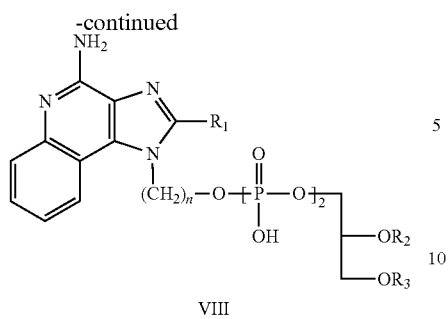

VIII

Imidazoquinoline diphosphate diglycerides VIII were prepared by coupling the imidazoquinoline monophosphomorpholidate VI, prepared in crude form from imidazoquinoline III, with 1,2-diacyl-sn-glycerol-3-phosphate sodium salt VII according to methods known in the art (*Biochim. Biophys. Acta* 1980, 619, 604, *J. Biol. Chem.*, 1990, 265(11), (6112-6117) *J. Org. Chem.* 1997, 62, 2144-2147) as follows: $POCl_3$ (2.0 eq) and imidazoquinoline III (1.0 eq) were added to trimethyl phosphate (0.38 M) at 0° C. After stirring 15 h at 0° C., the reaction mixture was partitioned between $H_2O$ and $Et_2O$ and the layers separated. The organic layer was extracted three times with $H_2O$ and the pH of combined aqueous layers was adjusted to pH 9 with aq $NH_4OH$. The aqueous solution was concentrated and dried under high vacuum and the residue obtained purified by chromatography on silica gel with $CHCl_3$-MeOH—$H_2O$-$Et_3N$ (gradient elution, 90:10:0.5:0.5→60:40:5:1). The product obtained was dissolved in dioxane (0.12M) at 50° C. and treated with 4N HCl (1.5 eq). The HCl salt that precipitated was collected, rinsed with dioxane, and dried under high vacuum. Morpholine (5.0 eq) was added to a suspension of the salt in 1:1 t-BuOH—$H_2O$ (0.5M) and the reaction mixture was heated to 90° C. and treated with a solution of 1,3-dicyclohexylcarbodiimide (DCC, 5.0 eq) in t-BuOH (0.33 M). After 1 h at 90° C., the cooled reaction mixture was partitioned between $H_2O$ and $Et_2O$ and the layers separated. The organic layer was extracted twice with $H_2O$ and the combined aqueous layers concentrated and dried under high vacuum. A suspension of the crude phosphomorpholidate VI obtained (1.5 eq) and VII (1.0 eq) in a small volume of pyridine was concentrated under vacuum, and then co-evaporated twice with toluene, and dried under high vacuum; this procedure was repeated twice more. 4,5-Dicyanoimidazole (DCI, 3.0 eq) was then added to a suspension of the dried solids in pyridine (0.10 M) and the reaction mixture was stirred at room temperature for 10 days. The resulting mixture was concentrated and the residue obtained partitioned between $H_2O$—$CH_2Cl_2$ and the layers separated. The aqueous layer was extracted twice with $CH_2Cl_2$ and the combined organic layers were dried ($Na_2SO_4$), and concentrated. Chromatography on silica gel with $CHCl_3$-MeOH—$H_2O$ (gradient elution, 90:10:0.5→70:30:2) afforded compound VIII as a colorless solid.

EXAMPLE 8 (L5)

Preparation of 4-Amino-1-[2-(1,2-dipalmitoyl-sn-glycero-3-diphospho)ethyl]-2-ethoxymethyl-1H-imidazo[4,5-c]quinoline (Compound (I), $R_1=CH_2OCH_2CH_3$, Y=W=X=O, n=2, m=2, $R_2=R_3=n-C_{15}H_{31}CO$)

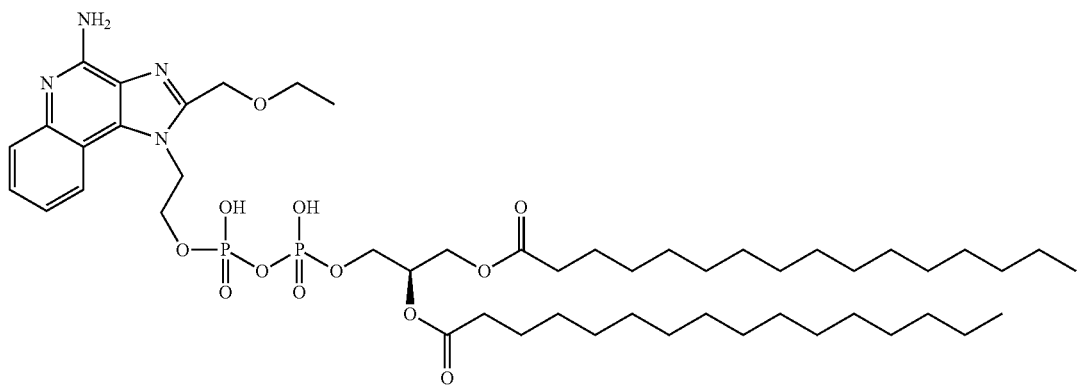 [SMILES: CCCCCCCCCCCCCCCC(=O)OC[C@H](COP(=O)(O)OP(=O)(O)OCCn1c(COCC)nc2c(N)nc3ccccc3c21)OC(=O)CCCCCCCCCCCCCCC]

Compound L5 was prepared in 22% yield following the general procedure described in Example 6 above: $^1H$ NMR ($CDCl_3$, 400 MHz): δ 8.17 (bs, 1H), 7.10-7.40 (2-3 m, 2-3H), 5.25 (bs, 1H), 4.60-5.00 (bm, 3H), 4.38 (m, 1H), 4.05-4.22 (m, 3H), 3.60-3.82 (m, 4H), 3.41 (bs, 1H), 3.10 (dd, 2H of $Et_3N$), 2.28 (m, 4H), 1.84 (dd, 1H), 1.56 (m, 5H), 1.25 (m, 54H), 0.88 (t, 7H); $^{13}C$ NMR ($CDCl_3$, 100 MHz): δ 173.5, 173.1, 152.4, 147.7, 135.8, 134.2, 128.8, 124.5, 123.6, 122.0, 118.8, 112.2, 77.2, 70.0, 68.1, 66.5, 63.8, 62.4, 54.6, 46.5, 45.5, 38.5, 33.9, 33.0, 29.5, 29.4, 29.1, 28.9, 28.7, 25.0, 24.6, 23.5, 22.7, 22.5, 14.6, 13.8, 13.7, 13.2, 10.7, 8.1. HRMS calcd for $[M+H]^+$ 997.5796, found 997.5776.

EXAMPLE 9

In Vivo Testing of Lipidated TLR7/8

TLR7/8 ligands may promote various aspects of the immune response in mice, noticeably the CD8 response. The difference in response between a TLR7/8 ligand (the "core" compound), and its corresponding lipidated derivative are investigated using techniques such as those described below.

Formulation of the compounds for a comparison study requires taking into account the different molecular weights of the core and lipidated molecules, (e.g. 45 and 4.5 µg of the lipidated compound L3 corresponds to approximately to 15 and 1.5 µg of the corresponding core compound, "L3 core"), allowing for the side by side comparison of the corresponding groups in the study. Higher doses of L3 (200 µg) and of L3 core (150 µg) are also tested. In one such study formulations summarized and described below (table 1) are used to vaccinate 6-8 week old C57BL/6 (H2 Kb), female mice (10/group). The mice receive two injections 14 days apart and are bled during weeks 1, 3 and 4 (for precise bleed days see FIG. 1). The mice are vaccinated intramuscularly. A heterologous prime/boost using recombinant adenovirus coding for the SIV-p27 protein and adjuvanted p27 are used as control groups, the adenovirus is injected at a dose of $5 \times 10^8$ VP. The study design is represented in FIG. 1.

TABLE 1

Summary of the formulations

| description | p27 | QS21 | MPL | SB62c [b] | L3 | L3 Core |
|---|---|---|---|---|---|---|
| QS/MPL (liposome based formulation) | 5 | 5 | 5 | — | — | — |
| QS/MPL + 200 µg L3 | 5 | 5 | 5 | — | 200 | — |
| QS/MPL + 45 µg L3 | 5 | 5 | 5 | — | 45 | — |
| QS/MPL + 4.5 µg L3 | 5 | 5 | 5 | — | 4.5 | — |
| QS/MPL + 150 µg L3 core | 5 | 5 | 5 | — | — | 150 |
| QS/MPL + 15 µg L3 core | 5 | 5 | 5 | — | — | 15 |
| QS/MPL + 1.5 µg L3 core | 5 | 5 | 5 | — | — | 1.5 |
| QS/MPL/SB62C (emulsion-based formulation) | 5 | 5 | — | 5 µl | — | — |
| QS/MPL/SB62C + 200 µg L3 | 5 | 5 | 5 | 5 µl | 200 | — |
| QS/MPL/SB62C + 45 µg L3 | 5 | 5 | 5 | 5 µl | 45 | — |
| QS/MPL/SB62C + 4.5 µg L3 | 5 | 5 | 5 | 5 µl | 4.5 | — |
| QS/MPL/SB62C + 150 µg L3 core | 5 | 5 | 5 | 5 µl | — | 150 |
| QS/MPL/SB62C + 15 µg L3 core | 5 | 5 | 5 | 5 µl | — | 15 |
| QS/MPL/SB62C + 1.5 µg L3 core | 5 | 5 | 5 | 5 µl | — | 1.5 |
| p27 | 5 | — | — | — | — | — |
| naive | — | — | — | — | — | — |

All compounds are in µg unless otherwise stated.
[b] SB62c contains the oil in water SB62 and cholesterol In the study design molecules are formulated in either a liposome-based or an oil-in-water-based adjuvant composition containing QS21 and MPL immunostimulants. To assess the added value of TLR7/8L, the innate and adaptive immune responses induced by the formulations containing the TLR7/8L, QS21 and MPL are compared to the one induced by the corresponding QS21 and MPL containing formulations.

The induction of antigen-specific CD8 and CD4 responses is assessed by measuring intracellular cytokines 7 days after the second injection. Peripheral blood lymphocytes (PBLs) are stimulated in the presence of a pool of peptides encompassing the whole p27 antigen (15-mers peptides, overlap by 11). The secretion of cytokines is blocked by Brefeldin A and the presence of 3 cytokines (IFNγ, TNFα and IL2) is evaluated by flow cytometry after intracellular staining with appropriate antibodies.

Figure 2:
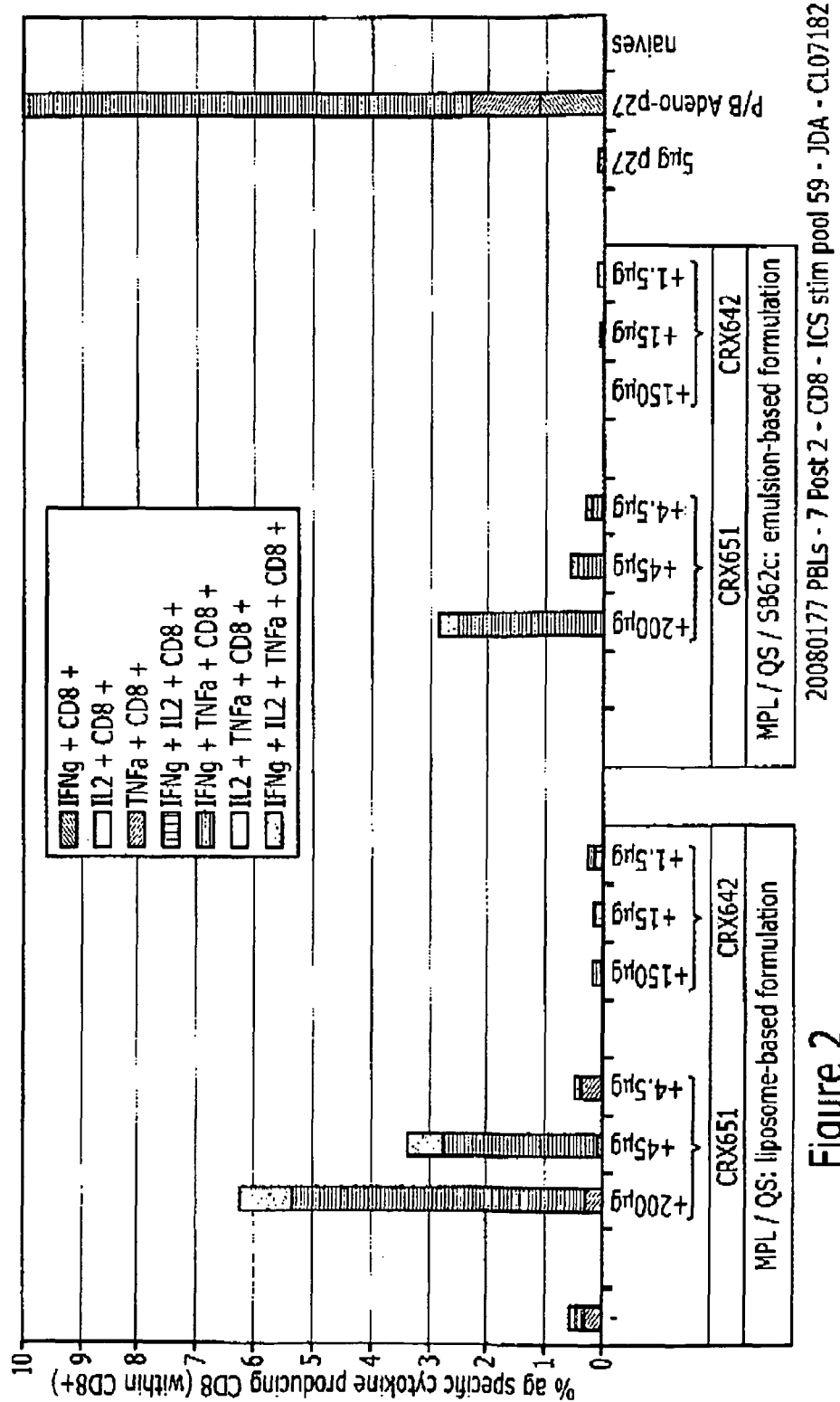
FIG. 2 shows the p27-specific CD8 response.
Figure 3:
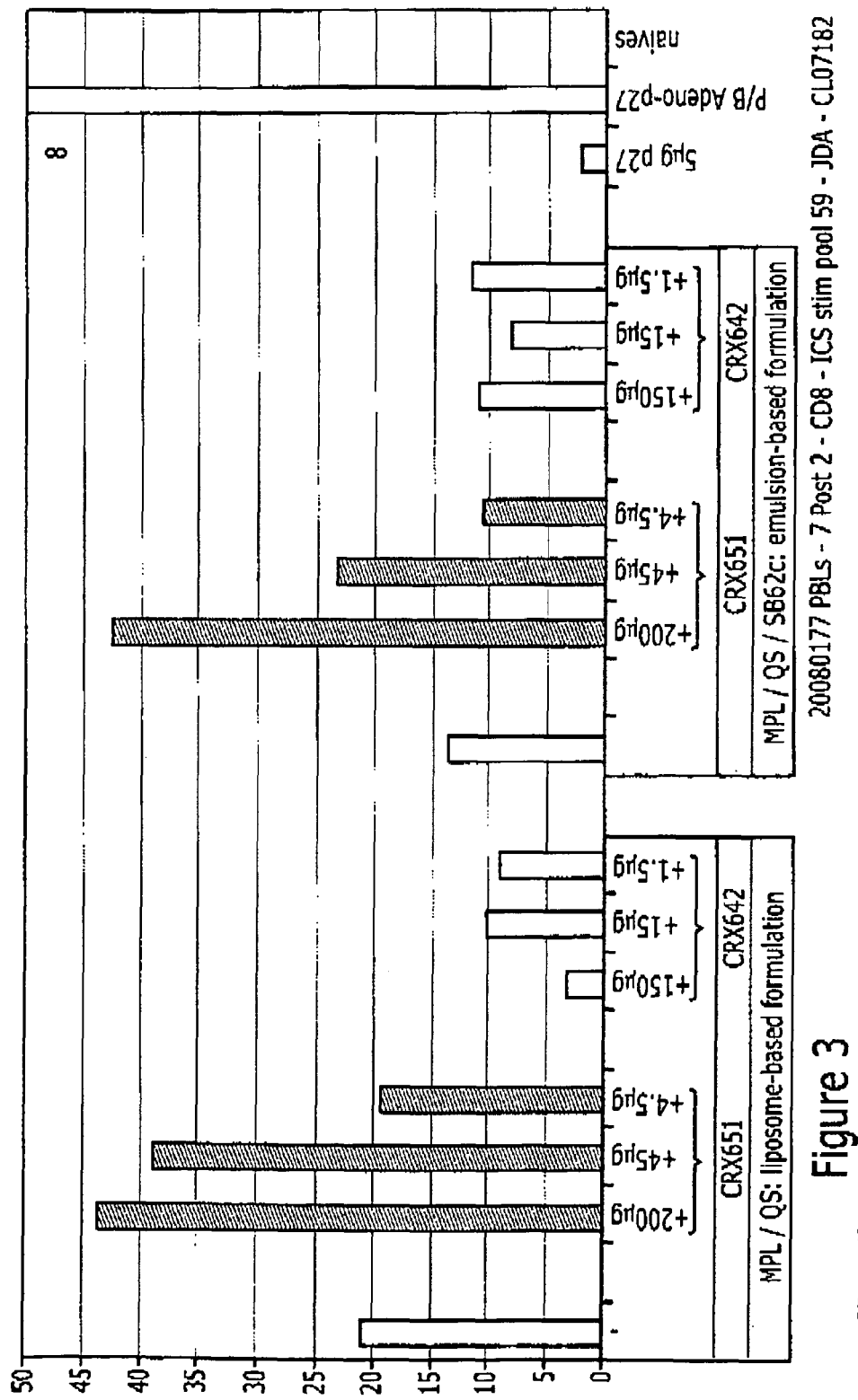
FIG. 3 shows p27-specific cytotoxic activity detected in vivo.

Studies similar to that described above were performed using CRX-642 and its lipidated counterpart L3. FIGS. 2 and 3 show the p27-specific T-cells frequency observed 7 days after the second immunization. In a dose response manner, the p27-specific CD8 frequency was clearly increased when liposomes containing L3 were co-administered with MPL and QS-21 formulations as compared to the control formulation without TLR7/8L (FIG. 2). Noticeably both the liposome-based formulation and the oil-in-water based formulations allowed for an increased in the CD8 response in presence of the lipidated TLR7/8L as compared to the corresponding control formulations without TLR7/8L. Furthermore the ability of generating cytokine-producing CD8 T cells was dependent on the lipidated nature of the TLR7/8 ligand, as the core molecule L3 core in contrast to L3 did not increase the response.

In complement to the evaluation of the induced CD8 response, antigen-specific cytotoxic activity may be assessed in vivo. Briefly, targets pulsed with p27 peptides spanning the whole protein and control unpulsed targets are injected into immunized mice and 24 hrs after injection, the p27-specific cytotoxicity is assessed by the disappearance of the pulsed target.

Complementary cytotoxic activity studies were performed with the evaluation of induced CD8 response of L3 core and L3 explained above. A higher cytotoxic activity was detected in mice immunized with lipidated TLR7/8 ligand-based formulations than with in mice receiving a core TLR7/8 ligand-based formulations (FIG. 3). This activity was higher than the one induced by control formulations based on QS21 and MPL only, especially when high doses of lipidated TLR7/8L were used.

Figure 4:
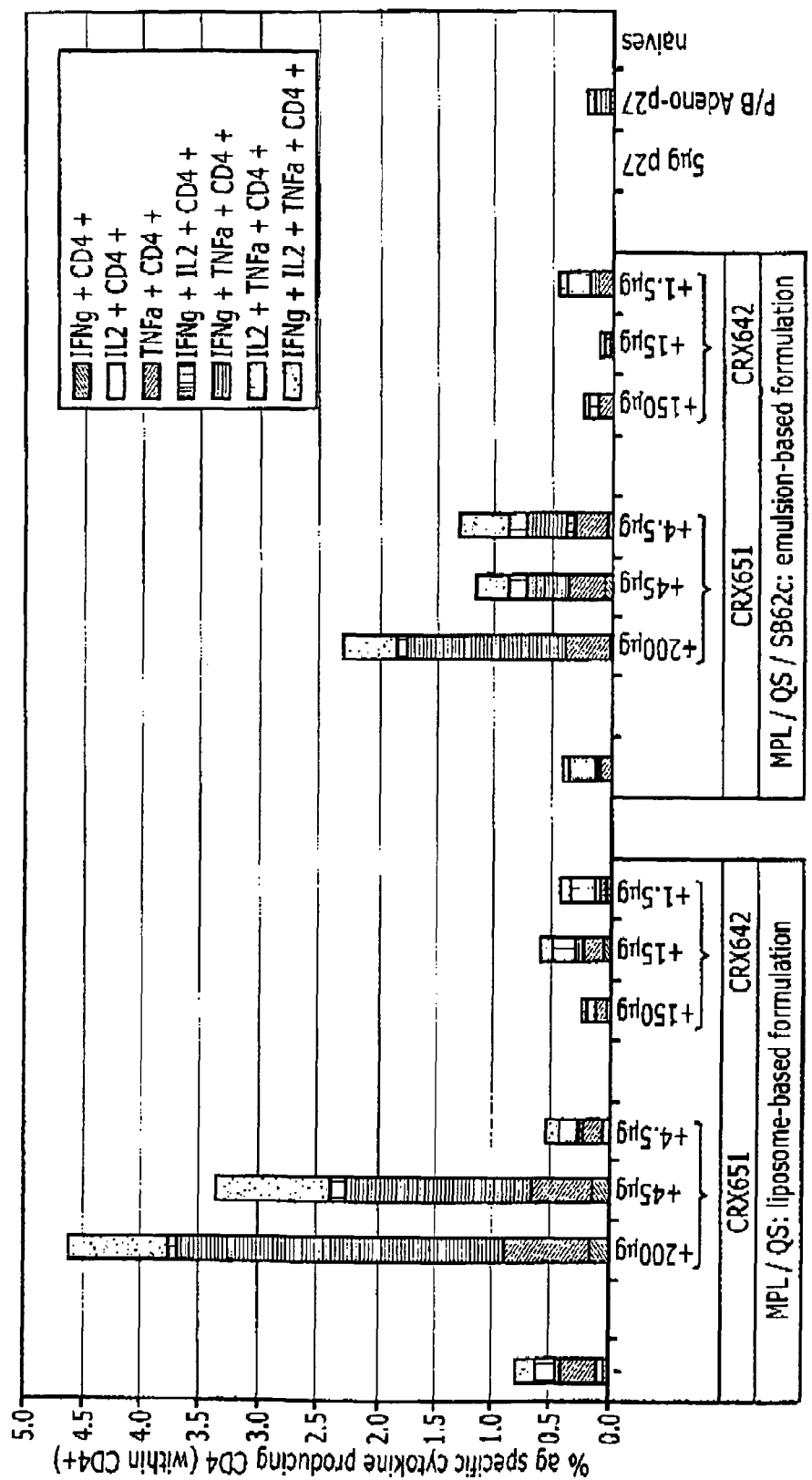
FIG. 4 illustrates the antigen-specific CD4 T cell response.

As shown for the CD8 response, the p27-specific CD4 frequency increased when liposomes containing L3 were co-administered with the liposome-based MPL and QS-21-containing formulation as compared to the control formulation, the response being dependent on the dose TLR7/8L injected (FIG. 4). As for the CD8 response, the core molecule L3 core was not able to induce a CD4 response over the one induced by the control formulations.

When administered in an emulsion-based formulation, the lipidated TLR7/8L was also able to increase the CD4 T-cell response over the level reached by the control formulation.

When lipidated, the added value of the TLR7/8 ligands within different formulations is shown by the increase up to 5-fold in cytokine-producing T cell frequency (both CD8 and CD4 T cells). Interestingly the cytokine profile of T-cell response was characterized by the high frequency of double positive T-cells (IFNγ[+] TNFα[+]).

Figure 5G:
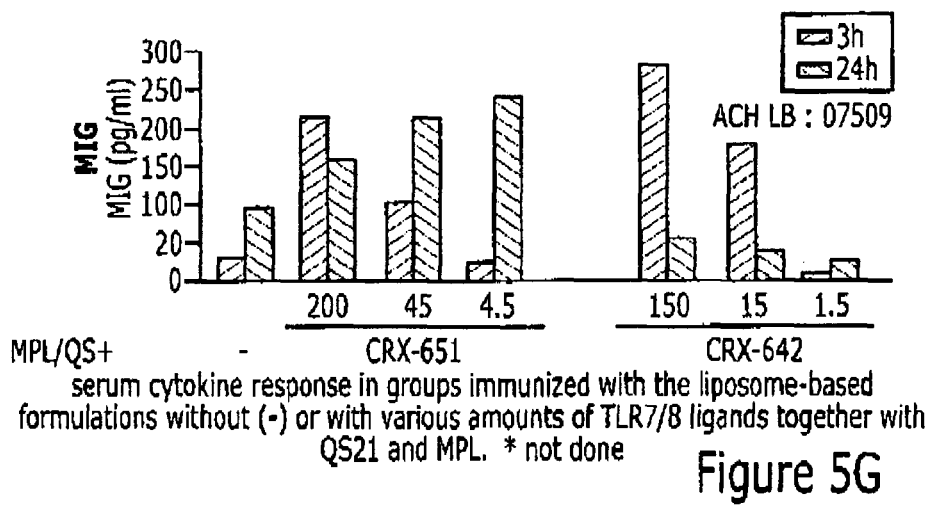
FIG. 5 shows serum cytokine response in groups immunized with the liposome-based formulations without (–) or with various amounts of TLR7/8 ligands together with QS21 and MPL.
Figure 6G:
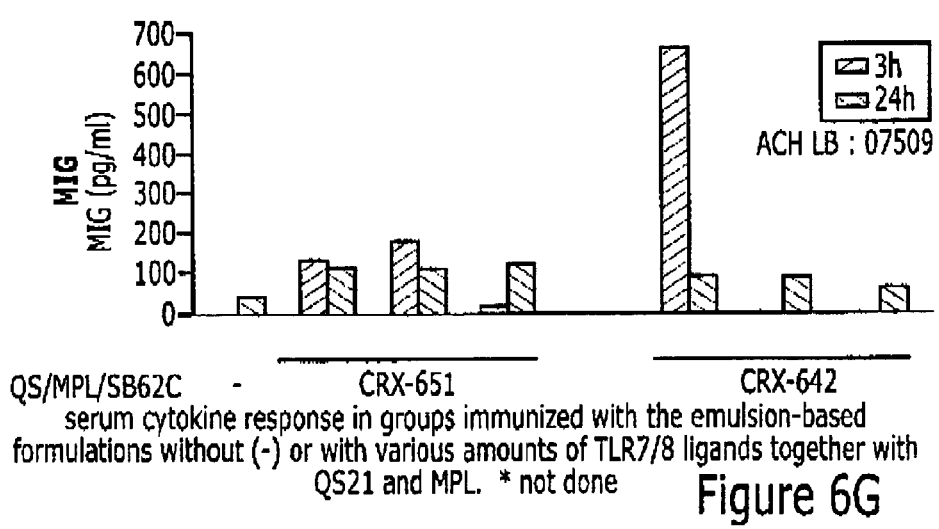
FIG. 6 shows serum cytokine response in groups immunized with the emulsion-based formulations without (–) or with various amounts of TLR7/8 ligands together with QS21 and MPL.

Additional investigation illustrates the ability of lipidated TLR7/8 compounds to induce innate chemokines and pro-inflammatory cytokines among which type I IFN is known to be required for the programming of naïve CD8-T-cell (survival, differentiate and memory development). These cytokines are measured in the sera of mice 3 and 24 hrs after the first injection (FIGS. 5 and 6).

Results of cytokine profiles for L3 core and L3 show similar profile of cytokines are observed between the liposome-based and emulsion-based formulations. TLR7/8 ligands are known to induce IFNα due to their ability to stimulate plasmacytoid dendritic cells and IFNα was indeed detected in the serum of mice immunized with L3 in a dose-dependent manner and at higher level than for its core counterpart, L3 core. Low IL-12p70 production, close to background level, was also detected. Level of INFγ increased at low dose of L3 while other inflammatory cytokines such as TNFα or IL-6 were enhanced when both L3 core and L3 were added to QS21 and MPL. The chemokines MCP-1 and MIG were both increased up to 10 fold with both compounds. Altogether, these data show that the tested lipidated molecule is as effective if not more potent than the corresponding core molecules to induce cytokine production in vivo.

What is claimed is:

1. A compound comprising Formula I

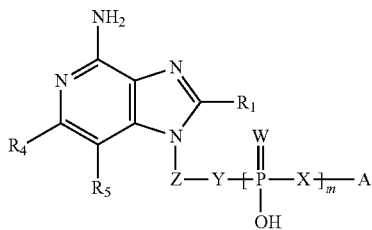

(I)

wherein
$R_1$=H, $C_{1-6}$ alkyl, $C_{1-3}$ alkoxy$C_{1-3}$ alkyl, $C_{3-6}$cycloalkyl$C_{1-3}$alkoxy, $C_{3-6}$cycloalkyl$C_{1-3}$alkyl
Z=$C_2$-$C_6$ alkyl or alkenyl, unsubstituted or terminally substituted by —(O—$C_2$-$C_6$alkyl)$_{1-6}$-
Y=O, NH
X=O, $CH_2$, $CF_2$
W=O or S
m=1-2,

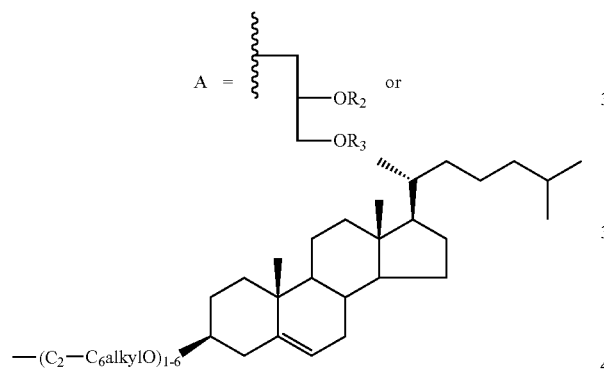

wherein
$R_2$=H or straight/branched/unsaturated $C_4$-$C_{24}$ alkyl or acyl
$R_3$=straight/branched/unsaturated $C_4$-$C_{24}$ alkyl or acyl
$R_4$, $R_5$=independently H, $C_1$-$C_6$alkyl, $C_1$-$C_6$ alkoxy, halogen, or trifluoromethyl; or taken together alternatively form a 6-membered aryl, heteroaryl containing one nitrogen atom, cycloalkyl, or heterocycloalkyl ring containing one nitrogen atom; unsubstituted or substituted by one or more of $C_1$-$C_6$alkyl, $C_1$-$C_6$ alkoxy, halogen, or trifluoromethyl, or pharmaceutically acceptable salts thereof.

2. A compound having Formula II

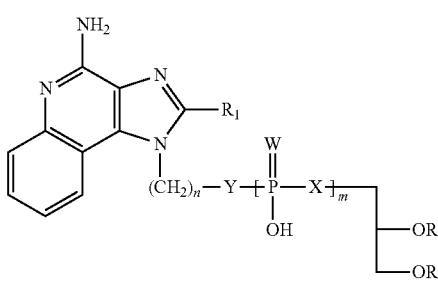

(II)

wherein
$R_1$=H, $C_{1-6}$ alkyl, $C_{1-3}$ alkoxy$C_{1-3}$ alkyl, $C_{3-6}$cycloalkyl$C_{1-3}$alkoxy, $C_{3-6}$cycloalkyl$C_{1-3}$alkyl
n=1-6
X=O, $CH_2$, $CF_2$
Y=O, NH
W=O or S
m=1-2,
$R_2$=H or straight/branched/unsaturated $C_4$-$C_{24}$ alkyl or acyl
$R_3$=straight/branched/unsaturated $C_4$-$C_{24}$ alkyl or acyl.

* * * * *

UNITED STATES PATENT AND TRADEMARK OFFICE
CERTIFICATE OF CORRECTION

PATENT NO. : 8,624,029 B2  
APPLICATION NO. : 13/125342  
DATED : January 7, 2014  
INVENTOR(S) : David A. Johnson Page 1 of 1

It is certified that error appears in the above-identified patent and that said Letters Patent is hereby corrected as shown below:

In the Specification

Column 1, Line 15, insert:
-- STATEMENT REGARDING FEDERALLY SPONSORED RESEARCH
This invention was made with government support under Contract # HHSN272200900036C awarded by the National Institutes of Health. The government has certain rights in the invention. --

Signed and Sealed this
Ninth Day of September, 2025

Coke Morgan Stewart
*Acting Director of the United States Patent and Trademark Office*